United States Patent
Kumagai et al.

(10) Patent No.: US 10,392,249 B2
(45) Date of Patent: Aug. 27, 2019

(54) HYDROGEN STORAGE CARBON MATERIAL

(71) Applicants: NATIONAL UNIVERSITY CORPORATION HOKKAIDO UNIVERSITY, Sapporo-shi, Hokkaido (JP); NATIONAL UNIVERSITY CORPORATION GUNMA UNIVERSITY, Maebashi-shi, Gunma (JP); NISSHINBO HOLDINGS INC., Tokyo (JP)

(72) Inventors: Haruo Kumagai, Sapporo (JP); Jun-ichi Ozaki, Kiryu (JP); Asao Oya, Kiryu (JP); Takafumi Ishii, Kiryu (JP); Takuya Maie, Chiba (JP); Rieko Kobayashi, Sano (JP); Yasuo Imashiro, Chiba (JP)

(73) Assignees: NATIONAL UNIVERSITY CORPORATION HOKKAIDO UNIVERSITY, Sapporo (JP); NATIONAL UNIVERSITY CORPORATION GUNMA UNIVERSITY, Maebashi (JP); NISSHINBO HOLDINGS INC., Tokyo (JP)

( * ) Notice: Subject to any disclaimer, the term of this patent is extended or adjusted under 35 U.S.C. 154(b) by 1 day.

(21) Appl. No.: 15/735,777

(22) PCT Filed: Jun. 17, 2016

(86) PCT No.: PCT/JP2016/068187
§ 371 (c)(1),
(2) Date: Dec. 12, 2017

(87) PCT Pub. No.: WO2017/010235
PCT Pub. Date: Jan. 19, 2017

(65) Prior Publication Data
US 2018/0179057 A1  Jun. 28, 2018

(30) Foreign Application Priority Data

Jul. 10, 2015 (JP) ................................. 2015-138774

(51) Int. Cl.
*C01B 3/00* (2006.01)
*C01B 32/00* (2017.01)
(Continued)

(52) U.S. Cl.
CPC ............ *C01B 3/0021* (2013.01); *B01J 20/20* (2013.01); *B01J 20/28* (2013.01);
(Continued)

(58) Field of Classification Search
CPC ......... C01B 3/00; C01B 3/0021; C01B 32/00; C01B 32/318; C01B 32/336; B01J 20/20;
(Continued)

(56) References Cited

U.S. PATENT DOCUMENTS 5,614,460 A  3/1997 Schwarz et al.
6,294,501 B1  9/2001 Chang
(Continued)

FOREIGN PATENT DOCUMENTS

JP  2004-529747 A  9/2004
JP  2006-335596 A  12/2006
(Continued)

OTHER PUBLICATIONS

Aug. 16, 2016 International Search Report issued in International Patent Application No. PCT/JP2016/068187.
(Continued)

*Primary Examiner* — Cam N. Nguyen
(74) *Attorney, Agent, or Firm* — Oliff PLC (57) ABSTRACT

A hydrogen storage carbon material having a carbon structure suited for hydrogen storage and a production method thereof. The hydrogen storage carbon material according to
(Continued)

this embodiment includes a carbon structure which has a ratio of an ultramicropore volume to a micropore volume of 60% or more, and in which stored hydrogen exhibits, in $^{1}$H-NMR measurement, a second peak at a position corresponding to a chemical shift of from −2 ppm to −20 ppm with respect to a first peak attributed to gaseous hydrogen.

6 Claims, 5 Drawing Sheets

(51) Int. Cl.
*C01B 32/318* (2017.01)
*C01B 32/336* (2017.01)
*B01J 20/20* (2006.01)
*B01J 20/28* (2006.01)
*G01N 24/08* (2006.01)

(52) U.S. Cl.
CPC ... *B01J 20/28011* (2013.01); *B01J 20/28071* (2013.01); *C01B 3/00* (2013.01); *C01B 32/00* (2017.08); *C01B 32/318* (2017.08); *C01B 32/336* (2017.08); *G01N 24/08* (2013.01); *C01P 2002/60* (2013.01); *C01P 2002/72* (2013.01); *C01P 2006/10* (2013.01); *C01P 2006/12* (2013.01); *C01P 2006/14* (2013.01); *C01P 2006/16* (2013.01); *C01P 2006/17* (2013.01); *Y02E 60/327* (2013.01)

(58) Field of Classification Search
CPC . B01J 20/28; B01J 20/28011; B01J 20/28071
See application file for complete search history.

(56) References Cited

U.S. PATENT DOCUMENTS

| | | | | |
|---|---|---|---|---|
| 8,404,384 B2* | 3/2013 | Feaver | ............ | H01M 4/583 |
| | | | | 429/231.8 |
| 8,475,687 B2* | 7/2013 | Fujii | ............ | B82Y 30/00 |
| | | | | 252/506 |
| 9,112,230 B2* | 8/2015 | Feaver | ............ | H01M 4/583 |
| 9,267,502 B2* | 2/2016 | Enami | ............ | F04B 35/04 |
| 9,306,217 B2* | 4/2016 | Yu | ............ | H01M 4/133 |
| 9,409,777 B2* | 8/2016 | Geramita | ............ | H01M 4/133 |
| 9,517,445 B2* | 12/2016 | Romanos | ............ | B01J 20/20 |
| 9,580,321 B2* | 2/2017 | Feaver | ............ | H01M 4/583 |
| 9,597,656 B2* | 3/2017 | Tour | ............ | B01J 20/2808 |
| 9,680,159 B2* | 6/2017 | Feaver | ............ | H01M 4/8615 |
| 9,985,289 B2* | 5/2018 | Costantino | ............ | H01B 1/04 |
| 10,141,122 B2* | 11/2018 | Feaver | ............ | H01G 11/34 |
| 10,147,950 B2* | 12/2018 | Sakshaug | ............ | H01M 4/0416 |
| 2005/0260118 A1* | 11/2005 | Lu | ............ | B01D 53/228 |
| | | | | 423/445 R |
| 2009/0246528 A1* | 10/2009 | Istvan | ............ | B82Y 30/00 |
| | | | | 428/403 |
| 2011/0052486 A1* | 3/2011 | Ito | ............ | B82Y 30/00 |
| | | | | 423/648.1 |
| 2011/0082024 A1* | 4/2011 | Liu | ............ | A61K 9/51 |
| | | | | 502/5 |
| 2011/0172087 A1* | 7/2011 | Tsao | ............ | C01B 3/0021 |
| | | | | 502/185 |
| 2012/0081838 A1* | 4/2012 | Costantino | ............ | H01B 1/04 |
| | | | | 361/502 |
| 2012/0313053 A1 | 12/2012 | Fujii et al. | | |
| 2013/0157151 A1* | 6/2013 | Feaver | ............ | H01M 4/583 |
| | | | | 429/405 |

FOREIGN PATENT DOCUMENTS

| | | |
|---|---|---|
| JP | 2009-249222 A | 10/2009 |
| JP | 2013-112572 A | 6/2013 |
| WO | 2002/059039 A1 | 8/2002 |
| WO | 2011/084994 A1 | 7/2011 |
| WO | 2011/105336 A1 | 9/2011 |
| WO | 2014/077714 A1 | 5/2014 |

OTHER PUBLICATIONS

Anderson et al; "NMR Methods for Characterizing the Pore Structures and Hydrogen Storage Properties of Microporous Carbons;" Journal of the American Chemical Society; Jun. 30, 2010; vol. 132 No. 25; pp. 8618-8626.

Dec. 19, 2018 Search Report issued in European Patent Application No. 16824215.4.

Centeno et al.; "Effects of phenolic resin pyrolysis conditions on carbon membrane performance for gas separation." Journal of Membrane Science; pp. 45-54; Jan. 2004; vol. 228, No. 1.

Jimenez et al.; "Hydrogen storage in different carbon materials: Influence of the porosity development by chemical activation." Applied Surface Science; pp. 2498-2509; Jan. 15, 2012; vol. 258, No. 7.

* cited by examiner

FIG.1

| | CARBONIZATION TEMPERATURE (°C) | SPECIFIC SURFACE AREA (m²/g) | MICROPORE VOLUME Vm (cm³/g) | ULTRAMICROPORE VOLUME Vum (cm³/g) | ULTRAMICROPORE RATIO Vum/Vm (%) |
|---|---|---|---|---|---|
| EXAMPLE 1 | 800 | 688 | 0.217 | 0.153 | 70.6 |
| EXAMPLE 2 | 1000 | 726 | 0.260 | 0.197 | 75.6 |
| EXAMPLE 3 | 1200 | 580 | 0.247 | 0.227 | 91.7 |
| COMPARATIVE EXAMPLE 1 | 600 | 553 | 0.218 | 0.102 | 46.8 |
| COMPARATIVE EXAMPLE 2 | 1500 | 227 | 0.220 | 0.048 | 21.6 |
| COMPARATIVE EXAMPLE 3 | 2000 | – | – | – | – |
| COMPARATIVE EXAMPLE 4 | 800 | 650 | 0.182 | 0.078 | 42.9 |
| COMPARATIVE EXAMPLE 5 | – | 1035 | 0.328 | 0.231 | 70.5 |

FIG.2

| | XRD PEAK TOP POSITION (2θ/°) | AVERAGE La (nm) | AVERAGE Lc (nm) | AVERAGE INTERLAYER SPACE $d_{002}$ (nm) |
|---|---|---|---|---|
| EXAMPLE 1 | 21.6 | 1.49 | 0.37 | 0.41 |
| EXAMPLE 2 | 22.1 | 1.75 | 0.41 | 0.40 |
| EXAMPLE 3 | 22.0 | 1.90 | 0.42 | 0.40 |
| COMPARATIVE EXAMPLE 1 | 18.2 | 0.89 | 0.34 | 0.49 |
| COMPARATIVE EXAMPLE 2 | 22.6 | 2.29 | 0.50 | 0.39 |
| COMPARATIVE EXAMPLE 3 | 24.4 | 3.32 | 0.62 | 0.36 |
| COMPARATIVE EXAMPLE 4 | 26.0 | 2.63 | 0.69 | 0.34 |
| COMPARATIVE EXAMPLE 5 | 24.0 | 2.49 | 0.43 | 0.36 |

FIG.3

| | BULK DENSITY (g/cm³) | TRUE DENSITY (g/cm³) | HYDROGEN STORAGE AMOUNT AT HYDROGEN PRESSURE OF 10 MPa (wt%) | HYDROGEN STORAGE AMOUNT PER UNIT SURFACE AREA ($\times 10^{-5}$ g/m²) | HYDROGEN STORAGE AMOUNT PER UNIT VOLUME (mg/cm³) | | CHEMICAL SHIFT OF ¹H-NMR PEAK (ppm) |
|---|---|---|---|---|---|---|---|
| | | | | | (BULK DENSITY) | (TRUE DENSITY) | |
| EXAMPLE 1 | 0.82 | 2.11 | 0.39 | 0.57 | 3.20 | 8.23 | -5.3 |
| EXAMPLE 2 | 0.88 | 2.12 | 0.42 | 0.58 | 3.70 | 8.90 | -7.4 |
| EXAMPLE 3 | 0.73 | 2.21 | 0.39 | 0.67 | 2.85 | 8.62 | -8.3 |
| COMPARATIVE EXAMPLE 1 | 0.71 | 1.42 | 0.29 | 0.52 | 2.06 | 4.12 | -1.6 |
| COMPARATIVE EXAMPLE 2 | 0.74 | 2.30 | 0.33 | 1.45 | 2.44 | 7.59 | -13.6 |
| COMPARATIVE EXAMPLE 3 | 0.64 | 1.36 | 0.02 | — | 0.13 | 0.27 | 0.0 |
| COMPARATIVE EXAMPLE 4 | 0.26 | 1.49 | 0.32 | 0.49 | 0.83 | 4.77 | -2.4 |
| COMPARATIVE EXAMPLE 5 | 0.59 | 1.66 | 0.37 | 0.36 | 2.18 | 6.14 | 0.0 |

HYDROGEN STORAGE CARBON MATERIAL

TECHNICAL FIELD

The present invention relates to a hydrogen storage carbon material.

BACKGROUND ART

Hydrogen is drawing attention as a clean energy source that does not generate carbon dioxide even when burnt. In order to utilize hydrogen as a fuel, a method of storing and transporting hydrogen has been investigated. As the method of storing and transporting hydrogen, a method involving using a high-pressure gas cylinder is generally used. However, the gas cylinder is heavy. In addition, storage efficiency per unit volume of the gas cylinder has a practical limit, and a significant increase in storage efficiency cannot be expected.

As a hydrogen storage method that replaces the gas cylinder, various materials have heretofore been investigated for hydrogen storage. For example, a method involving utilizing a hydrogen storage alloy has been known. However, the hydrogen storage alloy has a drawback in that the hydrogen storage alloy itself is heavy, and requires heat for releasing hydrogen. For these and other reasons, the range of application of the hydrogen storage alloy is limited. Therefore, there is a demand for development of a material that is more lightweight than the hydrogen storage alloy and that has high hydrogen storage capacity.

In this regard, Patent Literature 1 discloses a porous carbon material in which a volume of pores each having a diameter of 1 nm or less is more than 0.2 $cm^3/g$, and in which a ratio of the volume of the pores each having a diameter of 1 nm or less to a total pore volume is 85% or more.

CITATION LIST

Patent Literature

[Patent Literature 1] JP 2009-249222 A

SUMMARY OF INVENTION

Technical Problem

However, the related-art carbon material did not necessarily have a carbon structure suited for hydrogen storage.

The present invention has been made in view of the above-mentioned problem, and one of the objects of the present invention is to provide a hydrogen storage carbon material having a carbon structure suited for hydrogen storage, and a production method thereof.

Solution to Problem

In order to solve the above-mentioned problem, a hydrogen storage carbon material according to one embodiment of the present invention includes a carbon structure which has a ratio of an ultramicropore volume to a micropore volume of 60% or more, and in which stored hydrogen exhibits, in $^1$H-NMR measurement, a second peak at a position corresponding to a chemical shift of from −2 ppm to −20 ppm with respect to a first peak attributed to gaseous hydrogen. According to the one embodiment of the present invention, the hydrogen storage carbon material having a carbon structure suited for hydrogen storage is provided.

The hydrogen storage carbon material may be free of a metal inside. The carbon structure may have an average crystallite size La in an a-axis direction of 1.00 nm or more and 2.50 nm or less. The micropore volume may be 0.19 $cm^3/g$ or more and 0.40 $cm^3/g$ or less. The hydrogen storage carbon material may have a true density of 1.40 $g/cm^3$ or more and 3.00 $g/cm^3$ or less. The hydrogen storage carbon material may have a carbon structure exhibiting a peak having a peak top position of 18.0° or more and 25.0° or less in powder X-ray diffraction.

Advantageous Effects of Invention

According to the present invention, the hydrogen storage carbon material having a carbon structure suited for hydrogen storage and the production method thereof are provided.

DESCRIPTION OF EMBODIMENTS

Now, an embodiment of the present invention will be described. The present invention is not limited to examples shown in this embodiment.

A hydrogen storage carbon material according to this embodiment (hereinafter referred to as "carbon material of the present invention") includes a carbon structure which has a ratio of an ultramicropore volume to a micropore volume of 60% or more, and in which stored hydrogen exhibits, in $^1$H-NMR measurement, a second peak at a position corresponding to a chemical shift of from −2 ppm to −20 ppm with respect to a first peak attributed to gaseous hydrogen.

The carbon material of the present invention is a carbon material having hydrogen storage capacity. That is, the carbon material of the present invention is preferably applied to various apparatus and systems each utilizing hydrogen as a fuel. Therefore, this embodiment encompasses a use of the carbon material of the present invention in hydrogen storage, and a method of using the carbon material of the present invention for hydrogen storage. Hydrogen storage with the carbon material of the present invention is performed by, for example, bringing hydrogen to be used as a fuel into contact with the carbon material of the present invention at high pressure to cause the carbon material of the present invention to store the hydrogen. In addition, the hydrogen may be released from the carbon material of the present invention storing the hydrogen by decreasing the pressure of the hydrogen.

The carbon structure of the carbon material of the present invention contains micropores, and the micropores include ultramicropores. The micropores are pores each having a pore diameter of 2 nm or less (for example, a pore diameter measured by carbon dioxide adsorption of 0.48 nm or more and 2 nm or less). The ultramicropores are pores each having a pore diameter of 0.7 nm or less (for example, a pore diameter measured by carbon dioxide adsorption of 0.48 nm or more and 0.7 nm or less).

The carbon material of the present invention has such ultramicropores that the ratio of their ultramicropore volume to the micropore volume is 60% or more (60% or more and 100% or less). That is, in the carbon material of the present invention, the ultramicropores account for a relatively large ratio in the micropores.

The ratio of the ultramicropore volume to the micropore volume in the carbon material of the present invention is preferably 65% or more (65% or more and 100% or less), particularly preferably 70% or more (70% or more and 100% or less).

The carbon material of the present invention further has the carbon structure in which stored hydrogen shows, in $^1$H-NMR measurement, the second peak at a position corresponding to a chemical shift of from −2 ppm to −20 ppm with respect to the first peak attributed to gaseous hydrogen.

That is, an NMR spectrum obtained by $^1$H-NMR measurement of the carbon material of the present invention storing hydrogen contains the first peak attributed to gaseous hydrogen, and the second peak at a position shifted from the position of the first peak to a high magnetic field side by from 2 ppm to 20 ppm.

As described above, when the carbon material of the present invention storing hydrogen is subjected to $^1$H-NMR measurement, the second peak peculiar to the hydrogen adsorbed on the carbon material of the present invention, which is different from that of gaseous hydrogen (hydrogen gas), appears at a position corresponding to a chemical shift in the specific range.

The chemical shift of the second peak of the carbon material of the present invention may be, for example, from −3 ppm to −15 ppm, from −3 ppm to −12 ppm, from −4 ppm to −12 ppm, or from −4 ppm to −10 ppm.

As described above, the carbon material of the present invention has the peculiar carbon structure suited for hydrogen storage, which contains the ultramicropores at a high ratio, and in which stored hydrogen exhibits a chemical shift in the specific range. That is, the carbon material of the present invention has, at a high ratio, such ultramicropores that stored hydrogen exhibits a chemical shift in the specific range.

The carbon material of the present invention is produced by a method including heating a raw material containing an organic compound while increasing its temperature at a temperature increase rate of less than 50° C./h, and carbonizing the raw material at a temperature of 300° C. or more and 2,000° C. or less.

The organic compound contained in the raw material for the carbonization is not particularly limited as long as the organic compound can be carbonized (can be used as a carbon source), and an organic low-molecular-weight compound and/or an organic high-molecular-weight compound are/is used. Of those, an organic high-molecular-weight material is preferably used.

The organic high-molecular-weight compound is not particularly limited, and there may be used, for example, one or more kinds selected from a group consisting of a phenolic resin, polyacrylonitrile, polyvinylpyridine, a chelate resin, cellulose, carboxymethyl cellulose, polyvinyl alcohol, polyacrylic acid, polymethylacrylate, polymethylmethacrylate, polyfurfuryl alcohol, a furan resin, a phenol formaldehyde resin, polyimidazole, a melamine resin, an epoxy resin, pitch, lignite, polyvinylidene chloride, polycarbodiimide, lignin, anthracite, biomass, a protein, humic acid, polysulfone, polyaminobismaleimide, polyimide, polyaniline, polypyrrole, and an ionomer.

The carbonization is performed by heating the raw material and keeping the raw material at a predetermined temperature (carbonization temperature) at which the organic compound contained in the raw material is carbonized. The carbonization temperature is not particularly limited as long as the carbonization temperature is a temperature at which the organic compound contained in the raw material is carbonized. The carbonization temperature may be, for example, 300° C. or more and 2,000° C. or less, more than 600° C. and less than 1,500° C., or 700° C. or more and 1,400° C. or less.

A period of time for which the raw material is kept at the carbonization temperature is not particularly limited as long as the organic compound contained in the raw material is carbonized at the temperature. The period of time may be, for example, 5 minutes or more and 24 hours or less. The carbonization is preferably performed under a stream of an inert gas, for example, nitrogen.

In the carbonization in the production of the carbon material of the present invention, a relatively small temperature increase rate of less than 50° C./h is employed. Specifically, for example, when the carbonization temperature is 1,000° C. or less, the heating to the carbonization temperature may be performed at a temperature increase rate of less than 50° C./h, and when the carbonization temperature is more than 1,000° C., the heating to at least 1,000° C. may be performed at a temperature increase rate of less than 50° C./h.

The temperature increase rate may be, for example, 45° C./h or less. More specifically, the temperature increase rate may be, for example, 20° C./h or more and less than 50° C./h, 20° C./h or more and 45° C./h or less, or 30° C./h or more and 45° C./h or less.

In the production of the carbon material of the present invention, a relatively high carbonization temperature and a relatively small temperature increase rate are preferably adopted. That is, in the production of the carbon material of the present invention, for example, the raw material may be: heated while its temperature is increased at a temperature increase rate of less than 50° C./h; and carbonized at a temperature of more than 600° C. and less than 1,500° C., or may be: heated while its temperature is increased at a temperature increase rate of less than 50° C./h; and carbonized at a temperature of 700° C. or more and 1,400° C. or less.

When the carbonization is performed while the heating is performed at such small temperature increase rate, the carbon material of the present invention having the carbon structure suited for hydrogen storage as described above is efficiently produced.

The carbon material of the present invention may be free of a metal in the inside thereof. That is, in this case, the carbon material of the present invention is produced by a method including heating a raw material containing an organic compound and no metal while increasing its temperature at a temperature increase rate of less than 50° C./h, and carbonizing the raw material at a temperature of 300° C. or more and 2,000° C. or less.

The carbon material of the present invention may have a micropore volume of 0.19 cm$^3$/g or more and 0.40 cm$^3$/g or less. In this case, the micropore volume of the carbon material of the present invention may be, for example, 0.20 cm$^3$/g or more and 0.30 cm$^3$/g or less.

The carbon material of the present invention may have an ultramicropore volume of 0.12 cm$^3$/g or more and 0.39 cm$^3$/g or less. In this case, the ultramicropore volume of the carbon material of the present invention may be, for example, 0.12 cm$^3$/g or more and 0.36 cm$^3$/g or less, or 0.12 cm$^3$/g or more and 0.29 cm$^3$/g or less.

The carbon structure of the carbon material of the present invention may have an average crystallite size La (average La) in an a-axis direction of 1.00 nm or more and 2.50 nm or less. In this case, the average La of the carbon material of the present invention may be, for example, 1.10 nm or more and 2.40 nm or less, or 1.30 nm or more and 2.00 nm or less.

The average La corresponds to a diameter of a circle in a case where a plane formed by the two-dimensional spreading of a carbon network plane included in the carbon structure is approximated to the circle, and the average La indicates the degree of the spread of the plane. When the average La falls within any one of the above-mentioned ranges, the carbon structure of the carbon material of the present invention has a relatively small spread of the carbon network plane in the a-axis direction, and includes many edge surfaces formed by frequent disconnection of the carbon network plane.

The carbon structure of the carbon material of the present invention may have an average crystallite size Lc (average Lc) in a c-axis direction of 0.20 nm or more and 0.65 nm or less. In this case, the average Lc of the carbon material of the present invention may be, for example, 0.30 nm or more and 0.60 nm or less, or 0.35 nm or more and 0.45 nm or less.

The average Lc indicates the thickness in the c-axis direction of a group of carbon network planes stacked parallel to each other included in the carbon structure. When the average Lc falls within the above-mentioned range, the carbon material of the present invention has a carbon structure in which a stacking structure in the c-axis direction is developed. As the average Lc increases, the carbon material of the present invention has a carbon structure in which the stacking number of carbon network planes is larger.

The carbon structure of the carbon material of the present invention may have an average (002) interlayer space $d_{002}$ (average interlayer space $d_{002}$) of 0.35 nm or more and 0.50 nm or less. In this case, the average interlayer space $d_{002}$ of the carbon material of the present invention may be, for example, 0.37 nm or more and 0.45 nm or less, or 0.40 nm or more and 0.42 nm or less. The average interlayer space $d_{002}$ is an average distance between carbon (002) planes forming the carbon structure.

The carbon material of the present invention may have a specific surface area, determined by carbon dioxide adsorption, of 20 m$^2$/g or more and 1,000 m$^2$/g or less. In this case, the specific surface area of the carbon material of the present invention may be, for example, 200 m$^2$/g or more and 900 m$^2$/g or less, or 560 m$^2$/g or more and 800 m$^2$/g or less.

The carbon material of the present invention may have a bulk density of 0.60 g/cm$^3$ or more and 3.00 g/cm$^3$ or less.

In this case, the bulk density of the carbon material of the present invention may be, for example, 0.70 g/cm$^3$ or more and 1.50 g/cm$^3$ or less, or 0.72 g/cm$^3$ or more and 0.90 g/cm$^3$ or less.

The carbon material of the present invention may have a true density of 1.40 g/cm$^3$ or more and 3.00 g/cm$^3$ or less. In this case, the true density of the carbon material of the present invention may be, for example, 1.50 g/cm$^3$ or more and 2.50 g/cm$^3$ or less, or 2.10 g/cm$^3$ or more and 2.25 g/cm$^3$ or less.

The carbon material of the present invention may have a carbon structure exhibiting a peak having a peak top position of 18.0° or more and 25.0° or less in powder X-ray diffraction. That is, when the carbon material of the present invention is subjected to powder X-ray diffraction, a peak having a peak top position of 18.0° or more and 25.0° or less is observed in the diffraction angle 2θ range of from 18° or more to 26° or less. The peak top position may be, for example, 19.0° or more and 25.0° or less, or 21.0° or more and 23.0° or less.

The carbon material of the present invention may have a hydrogen storage amount, measured at 298 K and a hydrogen pressure of 10 MPa by a method in conformity with JIS H 7201, of 0.05 wt % or more. Specifically, the hydrogen storage amount of the carbon material of the present invention may be, for example, 0.30 wt % or more, or 0.33 wt % or more.

The carbon material of the present invention may have a hydrogen storage amount per unit surface area, calculated by dividing the above-mentioned hydrogen storage amount by the above-mentioned specific surface area, of $0.40 \times 10^{-5}$ g/m$^2$ or more. Specifically, the hydrogen storage amount per unit surface area of the carbon material of the present invention may be, for example, $0.46 \times 10^{-5}$ g/m$^2$ or more, or $0.53 \times 10^{-5}$ g/m$^2$ or more.

The carbon material of the present invention may have a hydrogen storage amount per unit volume, calculated by dividing the above-mentioned hydrogen storage amount by the above-mentioned bulk density, of 0.50 mg/cm$^3$ or more. Specifically, the hydrogen storage amount per unit volume of the carbon material of the present invention based on the bulk density may be, for example, 1.00 mg/cm$^3$ or more, or 2.80 mg/cm$^3$ or more.

The carbon material of the present invention may have a hydrogen storage amount per unit volume, calculated by dividing the above-mentioned hydrogen storage amount by the above-mentioned true density, of 1.00 mg/cm$^3$ or more. Specifically, the hydrogen storage amount per unit volume of the carbon material of the present invention based on the true density may be, for example, 5.00 mg/cm$^3$ or more, or 8.20 mg/cm$^3$ or more.

Next, specific Examples according to this embodiment will be described.

EXAMPLES

[Production of Hydrogen Storage Carbon Material]

In Example 1, a hydrogen storage carbon material was produced by carbonizing a raw material containing an organic compound and being free of a metal. That is, beads each made of a phenolic resin (100 μm, manufactured by Gunei Chemical Industry Co., Ltd.) were heated under a vacuum to increase their temperature from room temperature to 800° C. at a temperature increase rate of 48° C./h, and were then kept at a carbonization temperature of 800° C. for 1 hour to be carbonized. After the carbonization, the temperature was lowered to room temperature by natural cooling. The obtained carbon material free of a metal in the inside thereof was used as a hydrogen storage carbon material according to Example 1. In Example 2, a hydrogen storage carbon material was produced in the same manner as in Example 1 described above except that the carbonization temperature was changed to 1,000° C.

In Example 3, beads each made of a phenolic resin (100 μm, manufactured by Gunei Chemical Industry Co., Ltd.) were heated under a vacuum to increase their temperature from room temperature to 1,000° C. at a temperature increase rate of 48° C./h, and further increase their temperature from 1,000° C. to 1,200° C. at a temperature increase rate of 100° C./h, and were then kept at a carbonization temperature of 1,200° C. for 1 hour to be carbonized. After the carbonization, the temperature was lowered to room temperature by natural cooling. The obtained carbon material free of a metal in the inside thereof was used as a hydrogen storage carbon material according to Example 3.

In Comparative Example 1, a hydrogen storage carbon material was produced in the same manner as in Example 1 described above except that the carbonization temperature was changed to 600° C. In Comparative Example 2, a hydrogen storage carbon material was produced in the same manner as in Example 3 described above except that the carbonization temperature was changed to 1,500° C. In Comparative Example 3, a hydrogen storage carbon material was produced in the same manner as in Example 3 described above except that the carbonization temperature was changed to 2,000° C.

In Comparative Example 4, a hydrogen storage carbon material was produced by carbonizing a raw material containing an organic compound and a metal. That is, 10 g of a phenolic resin, 3.05 g of iron phthalocyanine, and acetone serving as a solvent were mixed, and the resultant solution was dried to provide a solid. The solid was heated under a nitrogen atmosphere to increase its temperature from room temperature to 800° C. at a temperature increase rate of 10° C./min, and was then kept at a carbonization temperature of 800° C. for 1 hour to be carbonized. After the carbonization, the temperature was lowered to room temperature by natural cooling. The obtained carbon material was pulverized, and the carbon material pulverized and containing a metal (iron) inside was used as a hydrogen storage carbon material according to Comparative Example 4. Commercially available activated carbon (4H, manufactured by Tsurumi Coal Co., Ltd.) was used as a hydrogen storage carbon material according to Comparative Example 5.

[Measurement of Specific Surface Area]

$CO_2$ adsorption and desorption measurement was performed at 273 K. That is, the specific surface area, micropore volume, and ultramicropore volume of each of the carbon materials obtained as described above were measured using a high-pressure gas adsorption amount-measuring apparatus (BELSORP-HP, BEL Japan, Inc.).

Specifically, first, 1 g of a carbon material was kept at 300° C. and a pressure of 1 Pa or less for 2 hours to remove moisture adsorbed on the carbon material. Then, adsorption measurement in the $CO_2$ gas pressure range of from 0 MPa to 3.45 MPa was performed. With the use of the resultant adsorption isotherm, the specific surface area of the carbon material was calculated by a BET method. Further, the volume of micropores (pores each having a size of 2 nm or less) of the carbon material, and the volume of its ultramicropores (pores each having a size of 0.7 nm or less) were calculated by the HK method.

The HK method is a technique devised by Horvath and Kawazoe in order to determine the pore distribution of slit-shaped micropores, is capable of calculating a pore diameter distribution from an adsorption isotherm, and is considered to be effective for analysis of micropores ("Method for the Caluculation of Effective Pore Size Distribution in Molecular Sieve Carbon", Geza Horvath and Kunitaro Kawazoe, J. Chem. Eng. Japan, 16, 470 (1983)). Horvath and Kawazoe determined a change in free energy in a case in which a gap between graphite layers or a slit-shaped pore was filled with gas molecules, and expressed a relationship between a relative pressure and a distance between the graphite layers (slit-shaped pore) by the following equation:

$$RT \ln(P/P_0) = L(N_sA_s + N_aA_a)/(\sigma^4(l-d)) \times [\sigma^4/(3(l-d/2)^3) - \sigma^{10}/(9(l-d/2)^9) - \sigma^4/(3(d/2)^3) + \sigma^{10}/(9(d/2)^9)].$$

In the equation, R represents an ideal gas constant, T represents an absolute temperature, L represents Avogadro's number, $N_s$ represents the number of atoms per unit surface area of an adsorbent, $A_s$ represents the Lennard-Jones constant of an adsorbate, $N_a$ represents the number of molecules per unit surface area of the adsorbate in an adsorbed state, $A_a$ represents the Lennard-Jones constant for the adsorbate at zero interaction energy, l represents the interlayer distance of a slit-shaped pore (pore diameter), d represents the sum of the diameter dA (nm) of an adsorbate molecule and the diameter da (nm) of an adsorbent molecule, and σ represents a distance between an adsorbent surface and an adsorbate atom at zero interaction energy.

In analysis using analysis software included with the above-mentioned high-pressure gas adsorption amount-measuring apparatus analysis, a pore diameter was first determined, and then a relative pressure corresponding to the pore diameter was calculated. Next, an adsorption amount at the relative pressure was calculated by linear interpolation of the adsorption data obtained by the above-mentioned $CO_2$ adsorption and desorption measurement, and the resultant adsorption amount was plotted against the pore diameter to derive an integral curve. Then, the integral curve was differentiated to determine a pore distribution curve. From the result, the volume of micropores (pores of 2 nm or less), and the volume of ultramicropores (pores of 0.7 nm or less) were calculated. For the analysis, data for a low-pressure region (relative pressure of 0.530 or less) was used.

[Measurement of Bulk Density]

A weighed carbon material was gently placed in a dry graduated cylinder without being compressed. After that, the top surface of the powder layer was carefully leveled without being compressed, and its volume was read to the minimum scale unit to determine the bulk density (g/cm³) of the carbon material.

[Measurement of True Density]

A true density was measured at 25° C. by a gas replacement method through the use of a dry automatic densimeter (AccuPyc II 1340, manufactured by Micromeritics Instrument Corporation) and He gas.

[Powder X-ray Diffraction Measurement]

First, a sample of a carbon material was placed in a concave portion of a glass sample plate, and was pressed with a slide glass. Thus, the sample was uniformly loaded into the concave portion so that its surface and a reference surface were flush with each other. Then, the glass sample plate was fixed on a wide-angle X-ray diffraction sample stage so that the morphology of the loaded sample did not collapse. Then, powder X diffraction measurement of each sample was performed using an X-ray diffraction apparatus (Rigaku RINT2100/PC, Rigaku Corporation) to measure a diffraction peak, and integration was performed five times.

Thus, X-ray diffraction data to be analyzed was obtained. A voltage and a current applied to an X-ray tube were 50 kV and 300 mA, respectively, a sampling interval was 0.1° or 0.01°, a scanning rate was 1°/min, and a measurement angle range (2θ) was from 5° to 90°. In addition, a CuKα ray was used as an incident X-ray. Then, on the basis of the resultant X-ray diffraction pattern, the position of the top of a diffraction peak appearing in the diffraction angle 2θ range of from 18° or more to 26° or less was identified.

[Evaluation for Spread of Carbon Network Plane]

On the basis of the X-ray diffraction data obtained by the powder X-ray diffraction described above, evaluation for a crystallite size La was performed. That is, the average La and an La distribution were analyzed by using Diamond's method. For this analysis, software for analysis (Carbon Analyzer D series, Hiroyuki Fujimoto) installed in a computer was used. The data to be analyzed was limited to the eleven-band intensity of a carbon material measured using a CuKα ray as an X-ray source and using a counter graphite monochrometer. The maximum analyzable network plane size was about 7 nm.

The procedure of the analysis method proposed by Diamond is basically formed of the following six steps: (1) the measurement of the eleven-band intensity of a sample; (2) the correction of a measured intensity; (3) the assumption of model network planes expected to exist in the sample; (4) the calculation of theoretical scattering intensities from the assumed model network planes; (5) the least-square fitting of the determined measured intensity with the theoretical scattering intensities; and (6) the calculation of the weight fractions of the model network planes and an average network plane size from the weights of the respective theoretical scattering intensities. In view of the foregoing, first, the data to be analyzed was read, and was subjected to smoothing processing and absorption correction. The smoothing processing was performed with the number of smoothing points set to seven, and the absorption correction was performed using a theoretical absorption coefficient of 4.219.

Next, the theoretical scattering intensities were calculated. The following equation (I) was used as a calculation equation. In the equation (I), I represents the measured intensity, w represents a mass fraction, B represents a theoretical X-ray scattering intensity, P represents a polarization factor, and v and s each represent a network plane model factor.

$$I_{OBS} = \sum_{i=1}^{n} w_i B_i(s) + B^{-CH2-}(s) + B^{-CH3}(s) + B^{-NH2}(s) + B^{>C=O}(s) + B^{-O-}(s) + \sum P_r(s) + v(s) \quad (I)$$

In this case, all parameters can be represented as a function of n (see Hiroyuki Fujimoto, Carbon, 192 (2000) 125-129). The calculation of the theoretical scattering intensities requires, as the setting of initial conditions, the determination of a two-dimensional lattice constant $a_0$ and a Ruland coefficient, and the selection of the model network planes. The two-dimensional lattice constant is generally set to a value between the lattice constants of benzene and ideal graphite, i.e., from about 0.240 nm to about 0.24612 nm. The Ruland coefficient indicates the integration width of a function showing the pass band of the energy of the monochrometer used, and generally takes a value of from 0 to 1. In this analysis, 0.24412 nm, a value close to the lattice constant of a general carbon material, was selected as the initially set value of the two-dimensional lattice constant $a_0$, and 0.05 was selected as the initially set value of the Ruland coefficient.

Next, the model network planes were selected. The above-mentioned software can execute the calculation of a theoretical intensity using three kinds of model network planes, i.e., a benzene-coronene base model, a pyrene base model, and a mixed model. In this regard, in this analysis, the benzene-coronene base model was used. In the case of this model, the scattering intensity of a model network plane having a size of an odd-number multiple (×1, 3, 5 . . . 25, 27, 29) of the two-dimensional lattice constant $a_0$ (that is, the size is from about 0.25 nm to about 7 nm) can be calculated.

All selection conditions were determined as described above, and the theoretical scattering intensities were calculated. After the completion of the calculation, repeated calculation by the least-square method based on the following equation (II) was performed 1,000 times, and a measured profile and a theoretical profile were fitted with each other with a fitting angle range 2θ set to from 60° to 100°. After the completion of the fitting, the display of the computer displayed a fitting result, a network plane size distribution, and an average network plane size.

$$R = \frac{\sum_s \left| I_{os} - \sum_i \lambda_i B_{is} \right|}{\sum_s I_{os}} \times 100 \quad (II)$$

[Evaluation for Stacking Structure of Carbon Network Planes]

In addition, on the basis of the X-ray diffraction data obtained by the powder X-ray diffraction described above, evaluation for the stacking structure of carbon network planes in a carbon structure was performed. That is, an average Lc, the stacking number of carbon network planes and the distribution thereof, and an average interlayer space $d_{002}$ were analyzed using the above-mentioned software for analysis (Carbon Analyzer D series, Hiroyuki Fujimoto) installed in a computer.

In a calculation process using the software, the following five steps were performed: (1) the intensity correction of a diffraction line; (2) the correction of a background; (3) the calculation of a Patterson function; (4) the evaluation of validity by inverse Fourier transform; and (5) the calculation of the average Lc, an average stacking number, the stacking number distribution, and the average interlayer space $d_{002}$ using the Patterson function.

First, the diffraction data from 5° to 40° obtained by the X-ray diffraction measurement was subjected to the diffraction line intensity correction and the background correction. In the diffraction line intensity correction, a linear absorption coefficient μ of carbon was set to 4.219, a sample thickness t was set to 0.2 mm, a divergence slit width β was set to ⅔°, and a goniometer radius R was set to 285 mm. The background correction was performed by a spline interpolation method with base points set to around 15° and around 35°.

Then, to the corrected data, Hirsch's method was applied in the diffraction angle range of from 5° to 40° to calculate the Patterson function. Further, the resultant Patterson function was subjected to the inverse Fourier transform to reconstruct a diffraction pattern. Thus, the validity of the Patterson function was evaluated. The Hirsch's method is a method proposed by Hirsch in 1954 in order to evaluate the average stacking number and stacking number distribution of carbon network planes in a sample having a relatively small network plane size, such as coal or pitch.

The remaining calculation process was performed using the thus calculated Patterson function in accordance with the standard procedure of the software. Thus, the average Lc, the average stacking number, the stacking number distribution, and the average interlayer space $d_{002}$ were calculated.

[Measurement of Hydrogen Storage Amount]

A hydrogen storage amount at a hydrogen pressure of from 0 MPa to 11.5 MPa was measured at 298 K by a method in conformity to JIS H 7201. In addition, the obtained hydrogen storage amount (wt %) at a hydrogen pressure of 10 MPa was converted to a hydrogen storage amount (g) per 1 g of the carbon material, and the resultant value was divided by the bulk density or the true density to calculate a hydrogen storage amount per unit volume (mg/cm$^3$).

[$^1$H-NMR Measurement]

A sample of a carbon material was placed in a high-pressure NMR sample tube made of quartz. Then, piping for evacuation and gas introduction, and a valve were attached thereto, followed by degassing treatment at a temperature of 573 K and a final pressure of $1\times10^{-4}$ torr for 24 hours. The sample after the degassing treatment was quickly placed in a probe while in the reduced-pressure state. Hydrogen was introduced thereinto to 3.5 MPa, and the resultant was subjected to measurement. $^1$H-NMR measurement was performed using an FT-NMR apparatus having mounted thereon a high-pressure and temperature-variable probe (Apollo Pulse NMR Spectrometer, 38 MHz, manufactured by Tecmag Inc.). A 90° pulse method was adopted for a pulse sequence. A measurement temperature was set to 173 K. The position of a peak (first peak) attributed to gaseous hydrogen (hydrogen gas: gas-phase hydrogen present between sample particles), which increased when the sample of the carbon material was loaded in an amount corresponding to a half of the high-pressure NMR sample tube made of quartz, was used as a reference (0 ppm), and the chemical shift of a peak (second peak) shifted to a high magnetic field side with respect to the first peak was evaluated. Hydrogen present on the plane of an aromatic ring shifts to the high magnetic field side, that is, a low ppm side due to the effect of the ring current of the aromatic ring. The amount of the shift corresponds to the degree of the development of a carbon network plane structure, and hydrogen stored in a carbon material surface having a developed carbon network plane structure or in pores shows a large shift. Therefore, the second peak was considered to be attributed to hydrogen adsorbed on the carbon material, and its peak shift amount was considered to change in a manner dependent on a change in structure of a storage site.

[Results]

Figure 1:
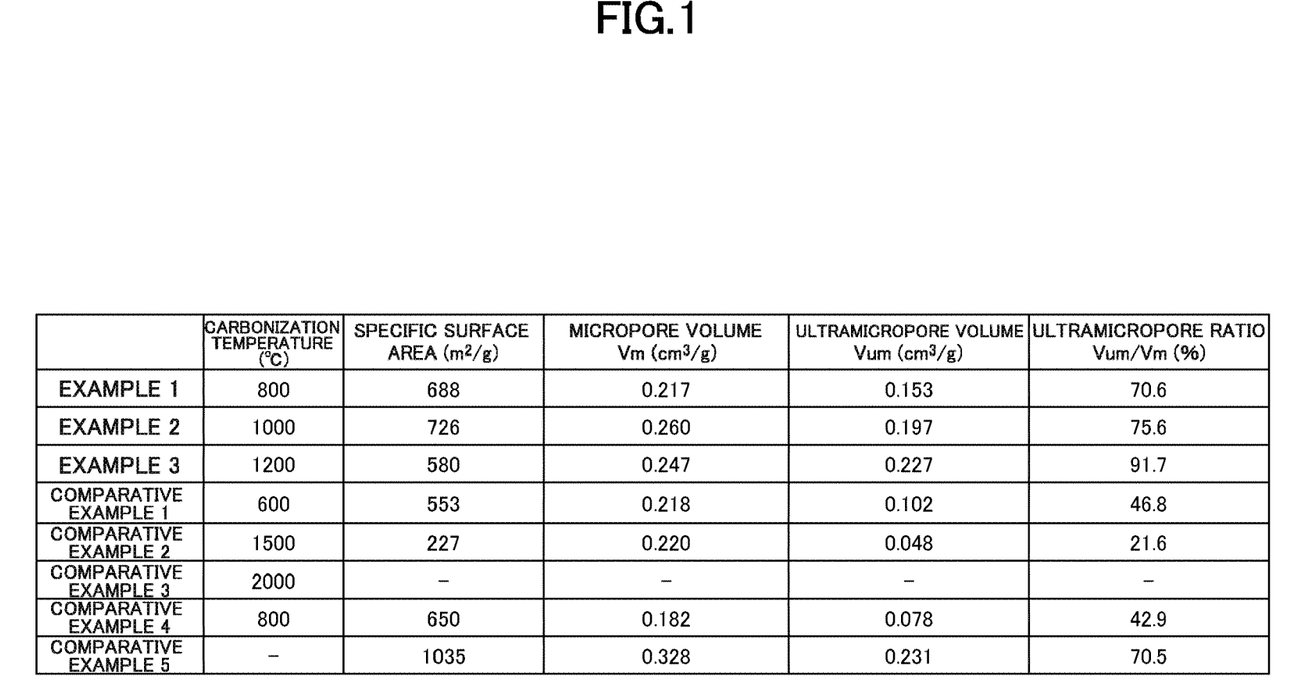
FIG. 1 is a table which shows the results of evaluation of characteristics, such as an ultramicropore volume, of carbon materials in Examples according to one embodiment of the present invention.

In FIG. 1, for each of the carbon materials according to Examples 1 to 3 and Comparative Examples 1 to 5, the carbonization temperature (° C.), the specific surface area (m$^2$/g), the micropore volume (cm$^3$/g), the ultramicropore volume (cm$^3$/g), and the ratio (%) of the ultramicropore volume to the micropore volume are shown. For the carbon material according to Comparative Example 3, the specific surface area and the pore volumes could not be appropriately measured. A possible reason for this is the possibility that the pore sizes were too small to be suited for the $CO_2$ adsorption and desorption measurement.

As shown in FIG. 1, the specific surface area measured by the BET method based on $CO_2$ gas adsorption was from 580 m$^2$/g to 726 m$^2$/g in Examples 1 to 3 where the carbonization temperature was from 800° C. to 1,200° C., and was larger than that in Comparative Examples 1 to 3 where the carbonization temperatures were 600° C., 1,500° C., and 2,000° C.

In addition, the ratio of the ultramicropore volume to the micropore volume in Examples 1 to 3 was from 70.6% to 91.7%, and was larger than that in Comparative Examples 1 to 5. That is, the micropores of each of the carbon materials according to Examples 1 to 3 included ultramicropores at a volume ratio of 70% or more and 95% or less.

Ultramicropores each having a size of 0.7 nm or less are suited for hydrogen storage at normal temperature. Therefore, it was considered that each of the carbon materials according to Examples 1 to 3 having a large ratio of the ultramicropores had a carbon structure particularly suited for hydrogen storage.

Figure 2:
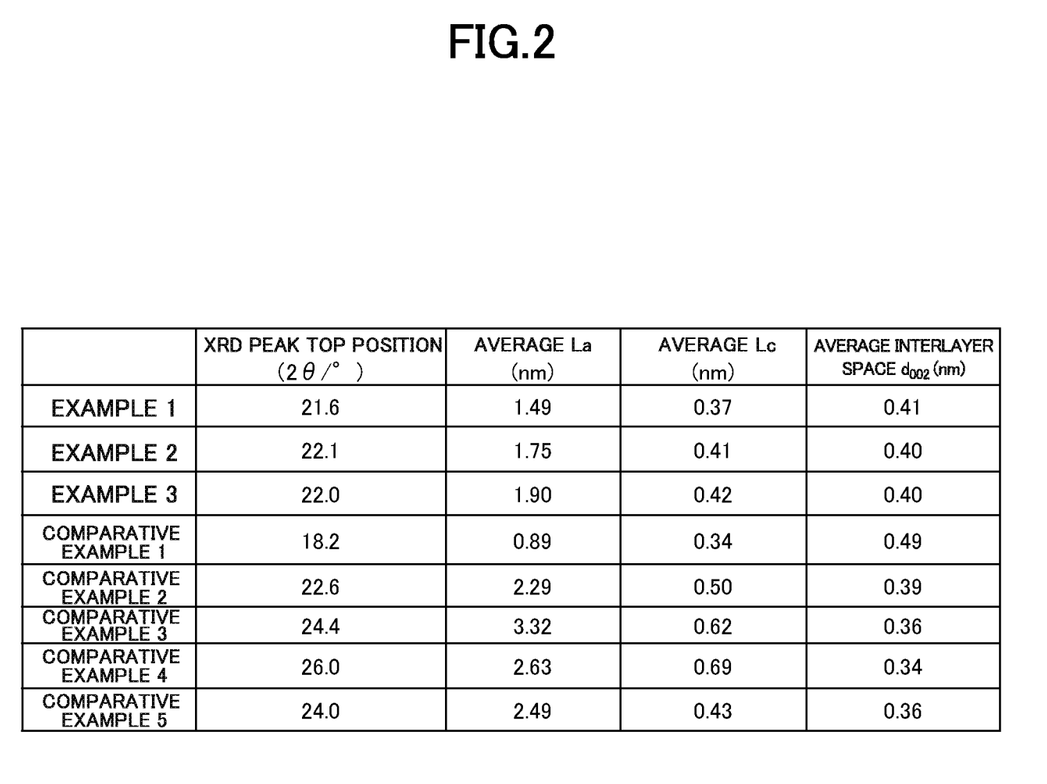
FIG. 2 is a table which shows the results of evaluation of characteristics, such as an average crystallite size La in an a-axis direction of a carbon structure, of carbon materials in Examples according to one embodiment of the present invention.

In FIG. 2, for each of the carbonmaterials according to Examples 1 to 3 and Comparative Examples 1 to 5, the XRD peak top position (2θ/°), the average La (nm), the average Lc (nm), and the average interlayer space $d_{002}$ (nm) are shown.

As shown in FIG. 2, the position of the top of the diffraction peak appearing in the diffraction angle 2θ range of from 18° to 26° obtained by the powder X-ray diffraction measurement (XRD peak top position) was from 21.6° to 22.1° in Examples 1 to 3. In contrast, the peak top positions in Comparative Examples 3 and 4 were 24.4° and 26.0°, respectively.

In this regard, a diffraction peak appearing at a diffraction angle 2θ of around 25° in X-ray diffraction is a peak derived from a carbon structure having high crystallinity. In this regard, as described above, the XRD peak top position of each of the carbon materials according to Examples 1 to 3 was less than 25°, and hence the crystallinity of each of the carbon materials was considered to be lower than those of the carbonmaterials according to Comparative Examples 3 and 4.

The carbon materials according to Examples 1 to 3 each had an average La of from 1.49 nm to 1.90 nm. That is, the spread of the carbon network planes in the a-axis direction of each of the carbon materials according to Examples 1 to 3 was relatively small, and it was considered that a large number of edges were formed by disconnection of the carbon network planes.

The carbon materials according to Examples 1 to 3 each had an average Lc of from 0.37 nm to 0.42 nm. In contrast, the carbon material according to Comparative Example 1 obtained by the carbonization at 600° C. had an average Lc of 0.34, which was smaller than those of Examples 1 to 3.

The carbon materials according to Comparative Examples 2 and 3 obtained by the carbonization at 1,500° C. or 2,000° C., and the carbon material according to Comparative Example 4 obtained by the carbonization of the raw material containing a metal each had an average Lc of from 0.50 nm to 0.69 nm, which was larger than those of Examples 1 to 3. That is, it was confirmed that the stacking structure of the carbon network planes of each of the carbon materials according to Examples 1 to 3 was more developed than that of Comparative Example 1, but was less developed than those of Comparative Examples 2 to 4.

The carbon materials according to Examples 1 to 3 each had an average interlayer space $d_{002}$ of from 0.40 nm to 0.41 nm. In contrast, the carbon material according to Comparative Example 1 obtained by the carbonization at 600° C. had an average interlayer space $d_{002}$ of 0.49 nm, which was larger than those of Examples 1 to 3.

The carbon materials according to Comparative Examples 2 and 3 obtained by the carbonization at 1,500° C. or 2,000°

C., and the carbon material according to Comparative Example 4 obtained by the carbonization of the raw material containing a metal each had an average interlayer space $d_{002}$ of from 0.34 nm to 0.39 nm, which was smaller than those of Examples 1 to 3.

The activated carbon according to Comparative Example 5 had an average interlayer space $d_{002}$ of 0.36. That is, the average interlayer space $d_{002}$ of each of Comparative Examples 2 to 4 was comparable to that of the graphite crystal in Comparative Example 5, whereas the average interlayer space $d_{002}$ of each of Examples 1 to 3 was larger than those of the Comparative Examples 2 to 5. The average interlayer space $d_{002}$ of the carbon material according to Comparative Example 2 was even larger than those of the carbon materials according to Examples 1 to 3, and its crystallinity was considered to be lower.

Figure 3:
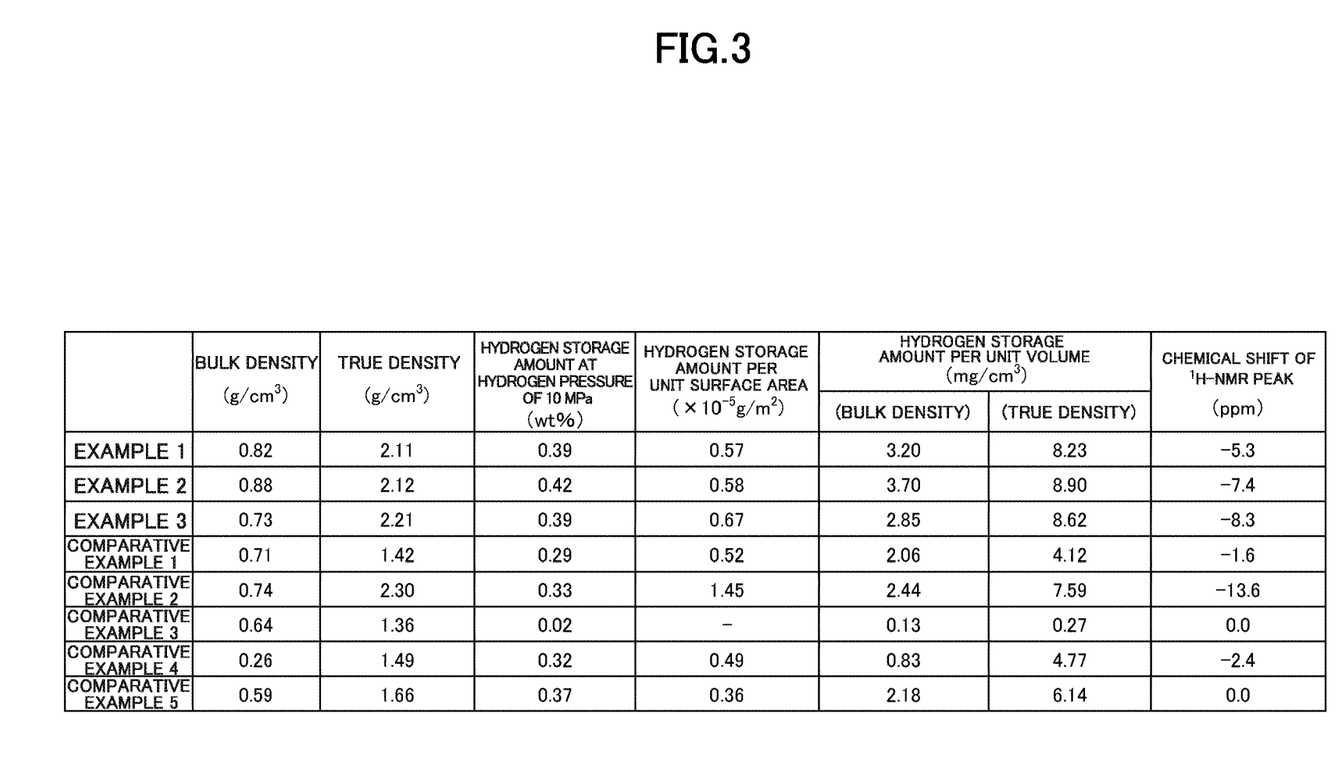
FIG. 3 is a table which shows the results of evaluation of characteristics, such as a chemical shift in $^1$H-NMR measurement, in Examples according to one embodiment of the present invention.

In FIG. 3, for each of the carbonmaterials according to Examples 1 to 3 and Comparative Examples 1 to 5, the bulk density (g/cm$^3$), the true density (g/cm$^3$), the hydrogen storage amount at a hydrogen pressure of 10 MPa (wt %), the hydrogen storage amount per unit surface area ($\times 10^{-5}$ g/m$^2$), the hydrogen storage amount per unit volume based on the bulk density or the true density (mg/cm$^3$), and the chemical shift (ppm) of a peak in $^1$H-NMR measurement are shown.

As shown in FIG. 3, the carbon materials according to Examples 1 to 3 each had a bulk density of from 0.73 g/cm$^3$ to 0.88 g/cm$^3$ and a true density of from 2.11 g/cm$^3$ to 2.21 g/cm$^3$, which were larger than those of Comparative Examples 1 and 3 to 5. The carbon materials according to Examples 1 to 3 each had a hydrogen storage amount of from 0.39 wt % to 0.42 wt %, which was larger than those of the carbon materials according to Comparative Examples 1 to 5.

The carbon materials according to Examples 1 to 3 each had a hydrogen storage amount per unit surface area of from $0.57 \times 10^{-5}$ g/m$^2$ to $0.67 \times 10^{-5}$ g/m$^2$, which was larger than those of Comparative Examples 1, 4, and 5. The carbon materials according to Examples 1 to 3 each had a hydrogen storage amount per unit volume based on the bulk density of from 2.85 mg/cm$^3$ to 3.70 mg/cm$^3$, and a hydrogen storage amount per unit volume based on the true density of from 8.23 mg/cm$^3$ to 8.90 mg/cm$^3$, which were both significantly larger than those of the carbon materials according to Comparative Examples 1 to 5.

Figure 4A:
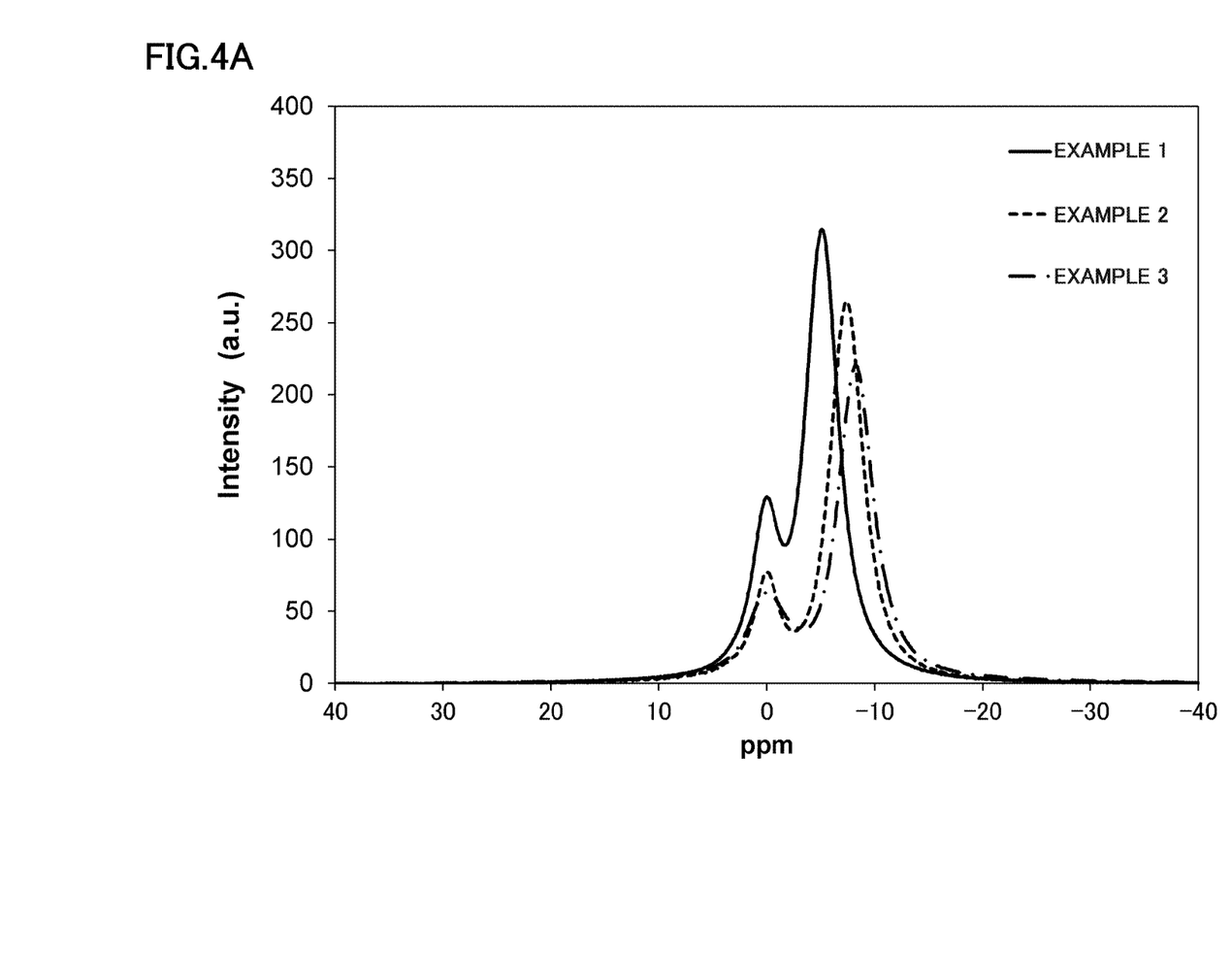
FIG. 4A is an explanatory diagram which shows examples of NMR spectra obtained by $^1$H-NMR measurement in Examples according to one embodiment of the present invention.
Figure 4B:
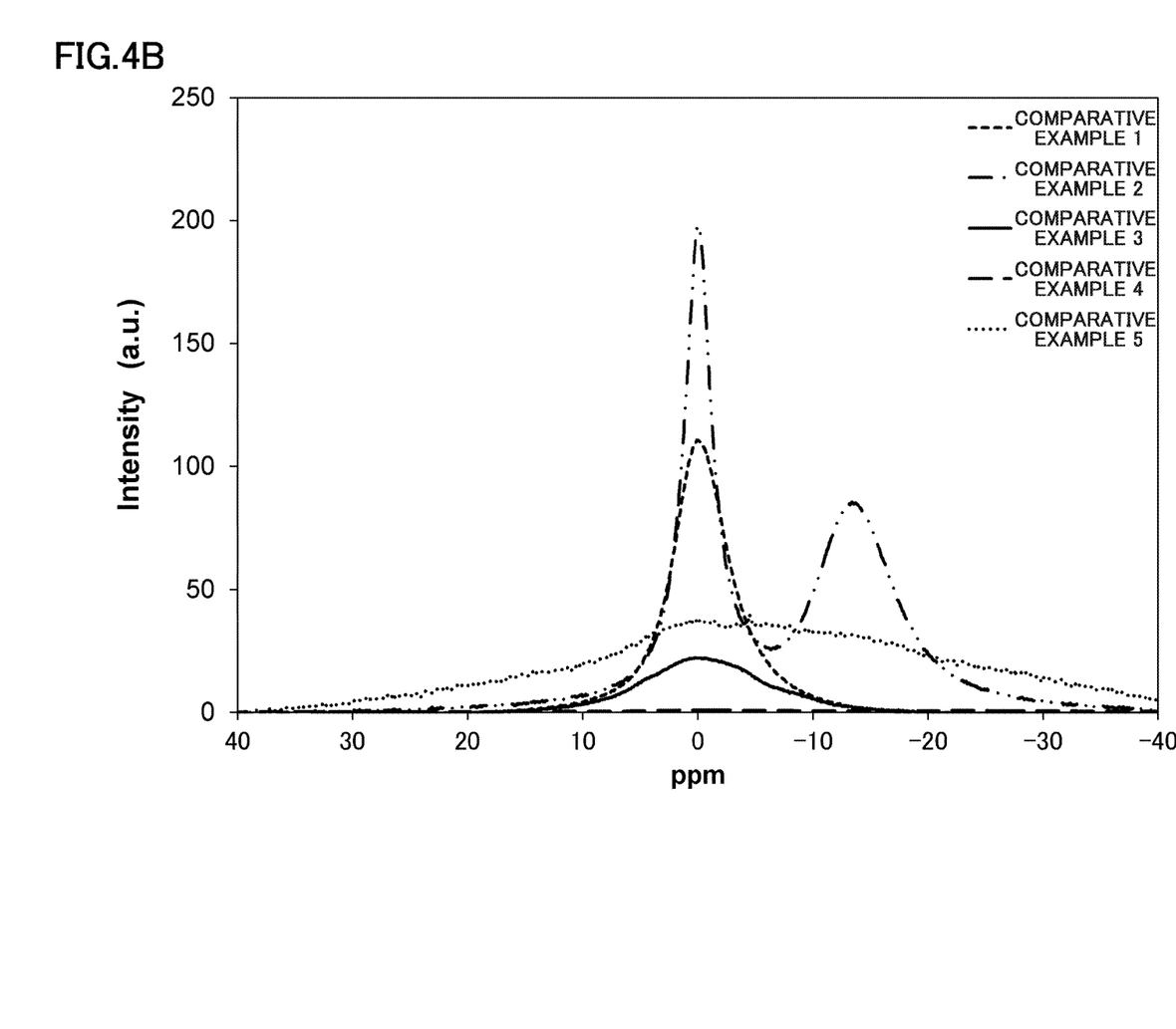
FIG. 4B is an explanatory diagram which shows other examples of NMR spectra obtained by $^1$H-NMR measurement in Examples according to one embodiment of the present invention.

In FIG. 4A and FIG. 4B, for the carbon materials according to Examples 1 to 3 and the carbon materials according to Comparative Examples 1 to 5, respectively, the NMR spectra obtained by the Fourier transform of signals in $^1$H-NMR measurement are shown. In each of FIG. 4A and FIG. 4B, the axis of abscissa represents a chemical shift (ppm), and the axis of ordinate represents a signal intensity.

As shown in FIG. 4B, the hydrogen introduced into each of the carbon materials according to Comparative Example 1 and Comparative Example 3 exhibited, in the NMR spectrum, a single peak (first peak) as in the case of hydrogen gas alone. The first peak had a relatively small shift from the reference frequency, and hence was considered to be attributed to gaseous hydrogen (hydrogen gas) present in voids in the sample.

Meanwhile, as shown in FIG. 4A, the hydrogen introduced into each of the carbon materials according to Examples 1 to 3 exhibited, in addition to the first peak, a second peak at a position shifted to the high magnetic field side with respect to the first peak. The second peak had a relatively large chemical shift and was dependent on the hydrogen storage amount per unit surface area, and hence was considered to be attributed to hydrogen adsorbed on the carbon material.

As shown in FIG. 4B, in Comparative Example 2 also, the second peak was shown in addition to the first peak. However, as described above, the carbon material according to Comparative Example 2 had a small specific surface area and a small ratio of ultramicropores compared to those of the carbon materials according to Examples 1 to 3, and was considered not to sufficiently have a carbon structure suited for hydrogen storage.

In view of the foregoing, as one reason that the carbonmaterials according to Examples 1 to 3 each exhibited high hydrogen storage capacity, it was considered that the carbon materials each had a peculiar carbon structure suited for hydrogen storage.

The invention claimed is:

1. A hydrogen storage carbon material, comprising a carbon structure which has a ratio of an ultramicropore volume to a micropore volume of 60% or more, and in which stored hydrogen exhibits, in $^1$H-NMR measurement, a second peak at a position corresponding to a chemical shift of from −2 ppm to −20 ppm with respect to a first peak attributed to gaseous hydrogen.

2. The hydrogen storage carbon material according to claim 1, wherein the hydrogen storage carbon material is free of a metal inside.

3. The hydrogen storage carbon material according to claim 1, wherein the carbon structure has an average crystallite size La in an a-axis direction of 1.00 nm or more and 2.50 nm or less.

4. The hydrogen storage carbon material according to claim 1, wherein the micropore volume is 0.19 cm$^3$/g or more and 0.40 cm$^3$/g or less.

5. The hydrogen storage carbon material according to claim 1, wherein the hydrogen storage carbon material has a true density of 1.40 g/cm$^3$ or more and 3.00 g/cm$^3$ or less.

6. The hydrogen storage carbon material according to claim 1 wherein the carbon structure exhibits a peak having a peak top position of 18.0° or more and 25.0° or less in powder X-ray diffraction.

* * * * *